United States Patent [19]

McRae

[11] Plant 4,879

[45] Aug. 24, 1982

[54] LILY PLANT: LILIUM 'MATCHLESS'

[76] Inventor: Edward A. McRae, 36752 SE. Bluff Rd., Boring, Oreg. 97009

[21] Appl. No.: 200,970

[22] Filed: Oct. 27, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant, characterized by rapid and natural propagation in field cultivation, vigorous growth when forced under glass without excessive leaf scorch or bud abortion, high resistance to disease and high tolerance to virus. The plant has broad leaves and bears large clusters of medium to large size upright flowers of excellent form, long persistence, and characterized in particular by their brilliant orange unspotted color.

1 Drawing Figure

BACKGROUND AND BRIEF STATEMENT OF THE INVENTION

My new variety of lily plant is classified botanically as a Lilium hybrid and commercially as an upright Asiatic hybrid, division I-A in horticultural classification of the Genus Lilium adopted by the Royal Horticultural Society of London.

My new lily plant originated as a seedling selected from a group of seedlings at Sandy, Oreg. The seedlings were planted during a breeding program carried on by me at Oregon Bulb Farms at Sandy, Oreg. It originated from a cross made in 1968 and first flowered in 1970 among the seedling beds of test crosses at Oregon Bulb Farms.

The seed parent of the cross was Lilium 'Enchantment' (U.S. Plant Pat. No. 862). The pollen parent was Lilium 'Connecticut Lemon Glow' (not patented).

The breeding program had as its primary objectives the production of brilliantly-colored, upright-flowering lily cultivars which would perform well when forced into flower under glass throughout the year, in addition to meeting the requirements of vigor, disease resistance, and rapid natural propagation in field cultivation. Cultivars were sought which would be disease resistant, virus tolerant, and not susceptible to leaf scorch or bud abortion when forced under glass.

My new lily plant resulting from this cross is characterized by the desired rapid natural propagation and field condition in vigorous growth under forcing conditions and resistance to disease and virus.

The plant most closely resembles the older cultivar 'Enchantment' but differs from it and is superior to it because of its broader leaves and its brilliant unspotted flower color. Its flowers resemble those of Lilium 'Orange Glow' but have the advantage of being upright flowers rather than side facing.

My new variety of lily plant has been asexually reproduced by me and under my direction at Sandy, Oreg. Successive generations produced by bulb scale propagation and natural propagation from bulblets have demonstrated that the novel and distinctive characteristics of the new variety are fixed and hold true under asexual propagation from generation to generation.

DESCRIPTION OF THE DRAWING

My new variety of lily plant is illustrated in the accompanying photographic drawing which shows the plant, its foliage, and its buds, and the open bloom in full color. Also shown in particular is the brilliant unspotted orange color of the flower.

DESCRIPTION OF THE NEW VARIETY

The following is a detailed description of my new variety of Asiatic hybrid lily, with nomenclature according to *International Lily Register* (Royal Horticultural Society, London, 2nd Edition, 1969) and with color designations according to the Royal Horticultural Society Color Chart, published by the Royal Horticultural Society in 1966.

THE PLANT

Form: Bulbous monocotyledon.

Height: 70–85 cm (28–34").

Growth: Vigorous, with considerable strength.

Foliage: Abundant, about 80 to 100 leaves per stem.

Size of leaves: 6–8 cm ($2\frac{1}{2}$–3") long and 1.0–1.5 cm ($\frac{1}{3}$–$\frac{3}{4}$") wide.

Shape of leaves: Lanceolate.

Texture of leaves: Leaves entire, not serrated, glossy, smooth and glabrous.

Color of leaves, upperside: Deep glossy green.

Color of leaves, underside: Light to medium glossy green.

Ribs and veins of leaves: Typical monocotyledonous venation: light green parallel veins.

Color of bulbs: White.

Size of bulbs: Usual commercial size is 12–20 cm (5–8") in circumference; bulbs can reach much larger size if desired.

INFLORESCENCE

Compact raceme. Bulbs 12–15 cm in circumference produce about 9 buds. Inflorescence does not carry secondary buds.

Peduncle or pedicels not hairy.

Strength of inflorescence: Strong and wirey.

Color of inflorescence: Medium to dark green stems with reddish anthocyanin overlay.

THE BUD

Size: 7–9 cm (3–$3\frac{1}{2}$") long.

Form: Lanceolate with obtuse tip; typical of Asiatic lilies.

Opens slowly: Opens in about 1 hour in response to morning light; flowers further up the stem open on subsequent days over an interval of 1 to 2 weeks. Typical of Asiatic lilies.

Color of mature buds: Brilliant orange (RHS CC #30B)

THE FLOWER

Bloom: Late June or early July in western Oregon once in mid-season and profusely.

Size: Flower diameter is 14–18 cm ($5\frac{1}{2}$–7″). Inner tepals are 4–5 cm ($1\frac{3}{4}$″–2″) wide. Outer tepals are 2–3 cm ($\frac{3}{4}$–$1\frac{1}{4}$″) wide.

Shape when flower first opens: Bowl-shaped with recurving tepals.

Tepals recurve more as flower ages.

Tepal arrangement: Typical of the genus Lilium, with 6 entire imbircated tepals.

Color, outer tepal: Brilliant unspotted orange (Royal Horticultural Society Color Code #30 A/B to 32A).

Color, base of tepals: Brilliant unspotted orange, RHS CC #30 A/B to 32 A.

Color, inner tepal: Brilliant unspotted orange, RHS CC #30 AB to 32A.

Color, reverse of tepal: Brilliant unspotted orange, RHS CC #30 A/B to 32A.

Tepals remain on individual flowers 5–7 days; stem has flowers with tepals adhering for about 3 weeks.

Flower texture: Shiny, velvety. Not affected by hot or wet weather. Does not hang on and dry; tepals fall as flower ages.

Pedicels: Length: 5–8 cm (2–3″) (slender stalk). Sturdy and upright.

Color: Medium to dark green, overlaid with reddish anthocyanin.

Disease resistance: To Botrytis blight and to Fusarium bulb rot.

Fragrance: None.

Lasting quality: Flowers remain on plants for about three to four weeks. Flowers remain on cut-flower stems for about three weeks, with adequate light.

REPRODUCTIVE ORGANS

Stamens and anthers: Typical of genus Lilium. 6 Versatile anthers hang (singly) from 6 filaments.

Filaments: 5–6 cm (2″) long and light orange.

Pollen: Deep orange.

Pistil: 1, typical of genus Lilium. Style is 5–6 cm (2″) long.

Stigma: Small, 3-lobed, dark purple in color, velvety in texture.

Ovary: Typical of genus Lilium. Superior, 6-chambered, single ovary.

THE FRUIT

Fertile, and ovoid to oblong capsule with 6 chambers.

Color at maturity: Medium green overlaid with light purple; fades to soft brown when capsule splits open to release seeds.

I claim:

1. A new and distinctive variety of Asiatic hybrid lily plant substantially as herein shown and described, characterized by its rapid natural propagation in field cultivation, by its vigorous growth when forced under glass, by its resistance to disease and virus, by its broad leaves, and in particular by the brilliant orange, unspotted color of its upright flowers.

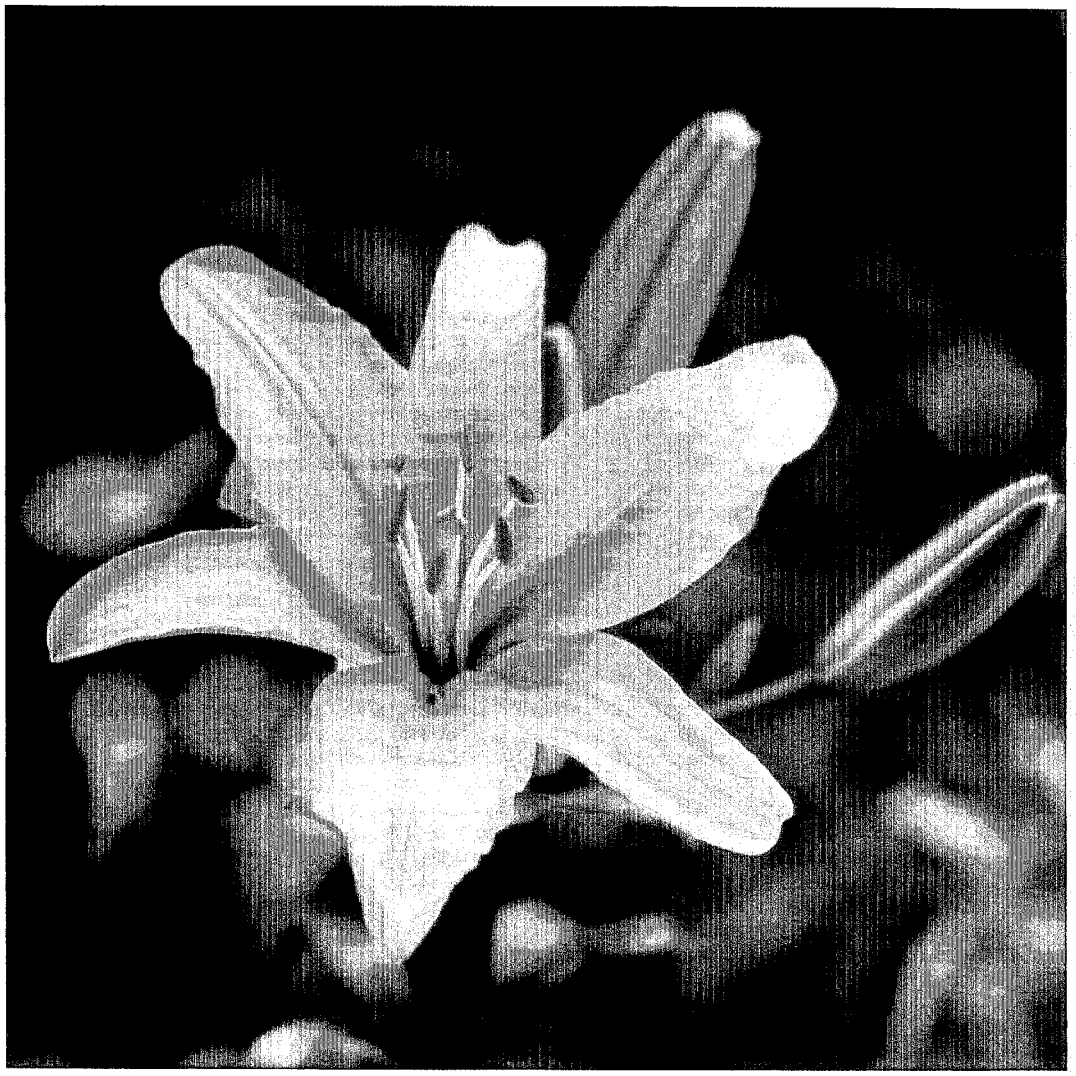

* * * * *